US010336975B2

(12) United States Patent
Kagawa et al.

(10) Patent No.: US 10,336,975 B2
(45) Date of Patent: Jul. 2, 2019

(54) CELL CULTURE BAG AND CELL CULTURE METHOD

(71) Applicant: FUJIFILM CORPORATION, Minato-ku, Tokyo (JP)

(72) Inventors: Hideaki Kagawa, Kanagawa (JP); Soichi Kohashi, Kanagawa (JP); Hidekazu Yamazaki, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 15/481,466

(22) Filed: Apr. 7, 2017

(65) Prior Publication Data

US 2017/0211028 A1    Jul. 27, 2017

Related U.S. Application Data

(63) Continuation of application No. PCT/JP2015/078671, filed on Oct. 8, 2015.

(30) Foreign Application Priority Data

Oct. 8, 2014  (JP) ................................ 2014-206988

(51) Int. Cl.
*C12M 3/00*     (2006.01)
*C12M 1/00*     (2006.01)
(Continued)

(52) U.S. Cl.
CPC ............ *C12M 23/14* (2013.01); *C12M 23/22* (2013.01); *C12M 23/24* (2013.01); *C12M 23/34* (2013.01); *C12M 23/48* (2013.01); *C12N 1/00* (2013.01)

(58) Field of Classification Search
CPC ...... C12M 21/02; C12M 23/14; C12M 23/24; C12M 23/28; C12M 23/40
See application file for complete search history.

(56) References Cited

U.S. PATENT DOCUMENTS 5,763,267 A  *  6/1998  Kurjan ................... C12M 23/26
                                                         435/293.1
6,071,859 A      6/2000  Ogawa et al.
(Continued)

FOREIGN PATENT DOCUMENTS

| CN | 1942575 A | 4/2007 |
|---|---|---|
| JP | 2005-295904 A | 10/2005 |
| KR | 20000005485 A | 1/2000 |

OTHER PUBLICATIONS

Extended European Search Report dated Sep. 26, 2017, issued in corresponding EP Patent Application No. 15849546.5.
(Continued)

*Primary Examiner* — Nathan A Bowers
(74) *Attorney, Agent, or Firm* — Solaris Intellectual Property Group, PLLC

(57) ABSTRACT

There is provided a cell culture bag including: plural tubular portions having gas permeability in which a tube axis direction is directed to a first direction and which are arranged side by side in a second direction intersecting with the first direction and are separated from each other using a partition wall; and communication portions having gas permeability which allow communication between two mutually adjacent tubular portions of the plural tubular portions in an intermediate region R between one end and the other end of the tubular portions.

21 Claims, 15 Drawing Sheets

(51) Int. Cl.
*C12N 1/00* (2006.01)
*C12M 1/04* (2006.01)

(56) References Cited

U.S. PATENT DOCUMENTS

| | | | | |
|---|---|---|---|---|
| 7,560,274 | B1* | 7/2009 | Fuller | C12M 23/24 |
| | | | | 383/102 |
| 2007/0113474 | A1* | 5/2007 | Everett | C12M 21/02 |
| | | | | 47/65.8 |
| 2007/0289206 | A1* | 12/2007 | Kertz | A01G 15/00 |
| | | | | 47/1.4 |
| 2008/0160591 | A1* | 7/2008 | Willson | C12M 21/02 |
| | | | | 435/132 |
| 2008/0274536 | A1 | 11/2008 | Hatano et al. | |
| 2009/0291490 | A1* | 11/2009 | Spradling | C12M 21/02 |
| | | | | 435/292.1 |
| 2011/0281339 | A1* | 11/2011 | Riley | C12M 21/02 |
| | | | | 435/257.1 |
| 2014/0186909 | A1* | 7/2014 | Calzia | C12M 23/22 |
| | | | | 435/134 |

OTHER PUBLICATIONS

English language translation of the following: Office action dated Mar. 15, 2018 from the KIPO in a Korean patent application No. 9-5-2018-018206732 corresponding to the instant patent application. This office action translation is submitted now in order to supplement the understanding of the cited regerence which is being disclosed in the instant information Disclosure Statement.

English language translation of the following: Office action dated Sep. 7, 2018 from the SIPO in a Chinese patent application No. 201580054974.0 corresponding to the instant patent application. This office action translation is submitted now in order to supplement the understanding of the cited references which are being disclosed in the instant information Disclosure Statement.

* cited by examiner

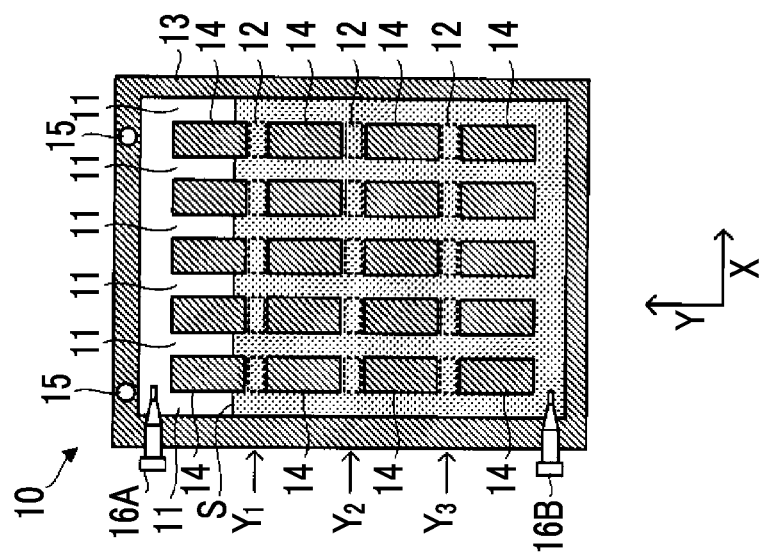

CELL CULTURE BAG AND CELL CULTURE METHOD

CROSS-REFERENCE TO RELATED APPLICATIONS

This application is a continuation application of International Application No. PCT/JP2015/078671, filed on Oct. 8, 2015, which is incorporated herein by reference in its entirety. Further, this application claims priority from Japanese Patent Application No. 2014-206988, filed on Oct. 8, 2014, the disclosure of which is incorporated by reference herein in its entirety.

BACKGROUND

Technical Field

The present invention relates to a cell culture bag and a cell culture method.

Description of the Related Art

In the related art, a stainless culture tank has been mainly used for expanded culture of cells. However, introduction of a plastic cell culture bag by which it is possible to reduce burden such as cleaning validation.

For example, a culture container of cells which is formed of plastic having gas permeability and in which the wall of the container is formed in a cylindrical shape, the cross-sectional surface is formed in any one of an angular cylindrical shape with a regular polygon shape, a spherical shape, and a hemispherical shape during culture is disclosed in JP2005-295904A.

It is considered that it is necessary to transplant $1 \times 10^9$ or more differentiated cells into a patient in order to treat, for example, hepatic disease or cardiac disease through cell transplantation. Therefore, development of mass culture technology of pluripotent stem cells is indispensable in order to realize the transplantation.

It is necessary to increase the volume of a cell culture bag in order to increase the scale of cell culture. However, when a cell suspension or a culture solution is stored in the cell culture bag by simply increasing the volume of the cell culture bag, the bottom portion of the cell culture bag is expanded and gas is insufficiently supplied to a center portion of the cell culture bag. In addition, in a case where a large amount of culture solution is stored, there is a problem of insufficient strength of the cell culture bag. A method for dividing a storage space of the cell culture bag into a plurality of regions is considered as a method for solving these problems. However, in this case, there is a concern that circulation of the cell suspension or the culture solution between the plurality of divided regions may be inhibited, and therefore, the environment of culturing cells between the plurality of divided regions may become inhomogeneous. As a result, there is a concern that the quality of cultured cells may become inhomogeneous despite the fact that the cells are cultured in the identical cell culture bag. According to a culture container disclosed in, for example, JP2005-295904A, the environment of culturing cells easily becomes inhomogeneous between a plurality of cylinders formed through heat sealing. In this manner, in the cell culture bag in the related art, it is difficult to culture a large amount of cells at the same lot as each other which are required for realizing treatment performed through cell transplantation and are guaranteed to have uniform quality.

SUMMARY

The present invention has been made in consideration of the above-described points and an object of the present invention is to provide a cell culture bag and a cell culture method in which it is possible to secure homogeneity of the culture environment of cells to be cultured even in a case where the scale of culturing cells is increased.

A cell culture bag according to the present invention includes: a plurality of tubular portions having gas permeability in which a tube axis direction is directed to a first direction and which are arranged side by side in a second direction intersecting with the first direction and are separated from each other using a partition wall; and communication portions which allow communication between two mutually adjacent tubular portions of the plurality of tubular portions in an intermediate region between one end and the other end of the tubular portions, and which have gas permeability.

In the cell culture bag according to the present invention, there may be two or more communication portions provided along the first direction in the two mutually adjacent tubular portions of the plurality of tubular portions.

In the cell culture bag according to the present invention, positions of the communication portions in the first direction may be aligned between the two mutually adjacent tubular portions. In addition, diameters of the tubular portions are may be the same as each other. In addition, diameters of the plurality of tubular portions and diameters of the communication portions may be the same as each other.

The cell culture bag of the present invention may be formed by pasting a plastic film having gas permeability. In this case, the partition wall may be formed by a plurality of seal portions formed on the plastic film. In addition, in the cell culture bag of the present invention, at least one of the plurality of seal portions may have a through hole. A width of the through hole may change along the first direction. It is preferable that a film formation flow direction during formation of the plurality of plastic films is coincident with the second direction. In addition, the plastic film may transmits visible light.

In the cell culture bag according to the present invention, three or more communication portions may be provided along the first direction in the two mutually adjacent tubular portions of the plurality of tubular portions. It is preferable that the diameters of the plurality of tubular portions are 5 mm to 50 mm and lengths of the plurality of tubular portions in the tube axis direction are shorter than or equal to 1000 mm.

The cell culture bag according to the present invention may further include a port which communicates with each of the plurality of tubular portions on at least one end side of each of the plurality of tubular portions in the first direction. In addition, the cell culture bag according to the present invention may further include a plurality of ports which communicate with each of the plurality of tubular portions on one end side and the other end side of each of the plurality of tubular portions in the first direction.

In a cell culture method according to the present invention, the cell culture bag is supported such that the tube axis directions of the plurality of tubular portions follow a vertical direction and at least one port is positioned on a lower side of the vertical direction, and cells are cultured by injecting a cell suspension or a culture solution from the port positioned on the lower side in the vertical direction.

In the cell culture method according to the present invention, the culture solution may be added to the cell culture bag by injecting the culture solution from the port positioned on the vertical direction. In this case, the culture solution may be added to the cell culture bag such that the surface of the culture solution after the addition reaches the position of the heights of the communication portions.

In the cell culture method according to the present invention, cells may be cultured while supporting the cell culture bag in a state where the cell culture bag is curved in a direction intersecting with the tube axis directions of the plurality of tubular portions such that the plurality of tubular portions are arranged in an annular shape.

In the cell culture method according to the present invention, cells may be cultured while supporting the cell culture bag using a support, which has a hook in a plurality of places in a circumferential direction and an axial direction and of which the axial direction is directed to a vertical direction, by surrounding the outer circumference of the support with the cell culture bag of which the tube axis directions of the plurality of tubular portions are directed to the vertical direction and inserting the hook into the through hole.

In the cell culture method according to the present invention, cells may be cultured while storing the cell culture bag in an airtight container.

In the culture method according to the present invention, cells may be cultured while maintaining the cell culture bag in a stationary state during a culture period.

According to the cell culture bag and the cell culture method of the present invention, it is possible to suppress deterioration of homogeneity of cells due to increase in the scale of the culture.

BRIEF DESCRIPTION OF THE DRAWINGS

FIG. 3C is a plan view of the cell culture bag according to the embodiment of the present invention after adding the culture solution to the cell culture bag.

DETAILED DESCRIPTION

Figure 1:
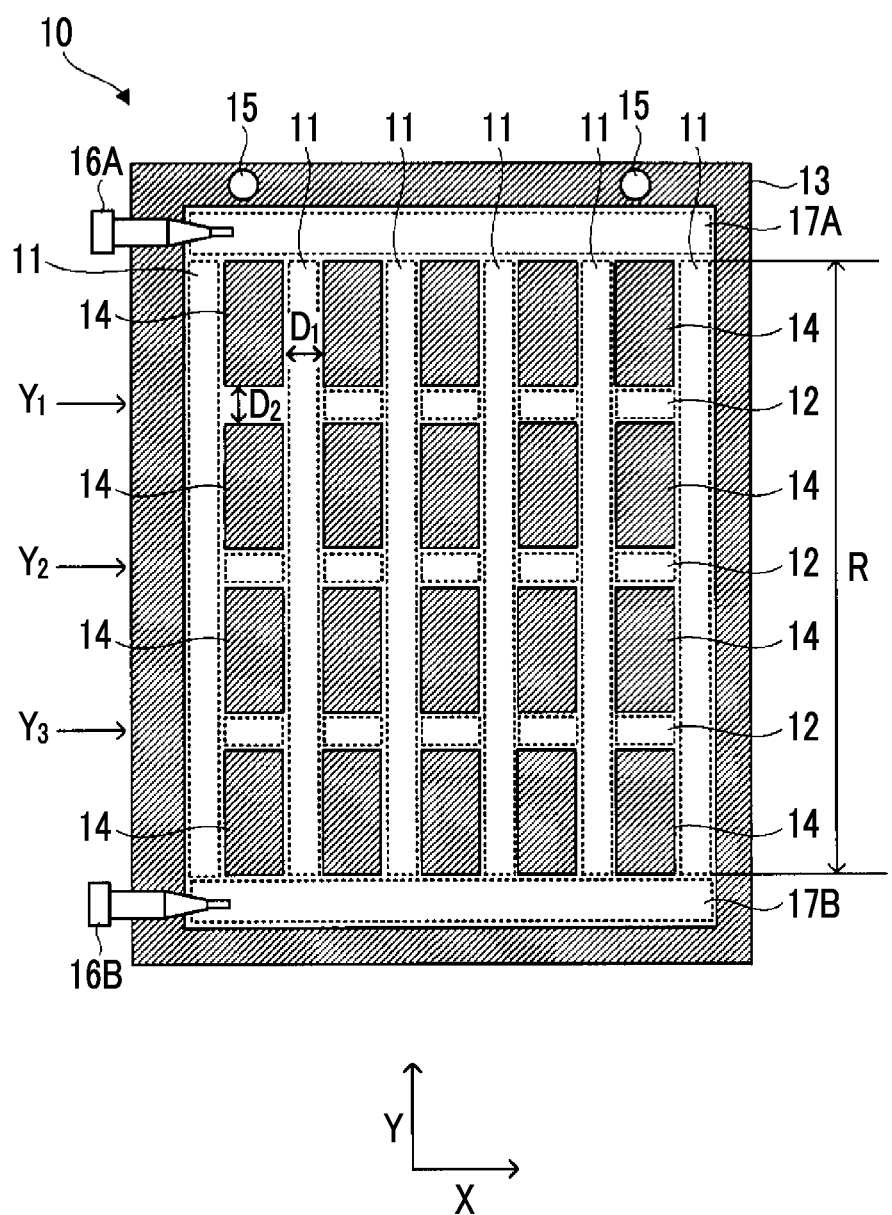
FIG. 1 is a plan view showing a configuration of a cell culture bag according to an embodiment of the present invention.

Hereinafter, an example of an embodiment of the present invention will be described while referring to drawings. The same reference numerals will be given to the same or equivalent components and portions in each drawing.

FIG. 1 is a plan view showing a configuration of a cell culture bag 10 according to an embodiment of the present invention. The cell culture bag 10 is formed by, for example, pasting two plastic films having flexibility and gas permeability through a technique such as heat sealing (thermocompression). One plastic film may be folded and pasted. In addition, the plastic film preferably transmits visible light in order to enable visual observation of cells cultured within the cell culture bag 10. It is possible to suitably use, for example, polyethylene or polypropylene as the plastic film constituting the cell culture bag 10.

The cell culture bag 10 has a plurality of tubular portions 11 which are separated from each other using partition walls consisting of seal portions 13 and 14. Here, the seal portions are referred to as portions where a plurality of films are pasted to each other. The plurality of tubular portions 11 are arranged side by side in a direction intersecting with a tube axis direction such that the tube axis directions become side by side to each other. The tube axis direction is referred to as an extending direction of a tubular portion 11 exhibiting a tubular shape. In FIG. 1, the tube axis direction of each of the tubular portions 11 is directed to a Y-axis direction and the plurality of tubular portions 11 are arranged side by side in an X-axis direction orthogonal to the Y-axis direction. An example of a configuration in which the cell culture bag 10 has six tubular portions 11 is shown in FIG. 1. The number of tubular portions 11 can be appropriately increased and decreased in accordance with the scale of culture.

The shape of a cross section of a tubular portion 11 is preferably circular, but may be elliptic or may not be completely circular.

The cell culture bag 10 has a plurality of communication portions 12 which allow communication between two mutually adjacent tubular portions 11 of the plurality of tubular portions 11 in an intermediate region R of the tubular portions 11. The intermediate region R is a region between one end and the other end of a tubular portion 11 in the tube axis direction. More specifically, the plurality of communication portions 12 are provided between two mutually adjacent tubular portions 11 along the tube axis direction (Y-axis direction) of the tubular portions 11 for each pair consisting of the two mutually adjacent tubular portions 11. In the example shown in FIG. 1, three communication portions 12 are provided at different positions between the two mutually adjacent tubular portions 11 in the Y-axis direction. However, at least one communication portion 12 may be provided between the two mutually adjacent tubular portions 11 along the tube axis direction (Y-axis direction).

The shape of a cross section of a communication portion 12 is preferably circular, but may be elliptic or may not be completely circular.

In the present embodiment, the positions of the three communication portions 12, which are provided between the two mutually adjacent tubular portions 11 along the Y-axis direction, in the Y-axis direction are arranged between pairs each consisting of the two mutually adjacent tubular portions 11. That is, the communication portions 12 are disposed at positions $Y_1$, $Y_2$, and $Y_3$ in the Y-axis direction so as to penetrate a plurality of tubular portions 11 in a straight line in the X-axis direction. In addition, in the present embodiment, diameters $D_1$ of the plurality of tubular portions 11 are the same as each other and diameters $D_2$ of the communication portions 12 are designed to be the same as the diameters $D_1$ of the tubular portions 11. The diameters $D_1$ of the tubular portions 11 and the diameters $D_2$ of the communication portions 12 are preferably 5 mm to 50 mm. In a case where the diameters $D_1$ of the tubular portions 11 and the diameters $D_2$ of the communication portions 12 are less than or equal to 50 mm, it is possible to sufficiently supply gas to a central portion of the tubular portions 11 and the communication portions 12 in a radial direction. In contrast, in a case where the diameters $D_1$ of the tubular portions 11 and the diameters $D_2$ of the communication portions 12 are set to be greater than or equal to 5 mm, circulation of a culture solution and a cell suspension stored in the cell culture bag 10 is secured, and therefore, it is possible to maintain homogeneity of culture environment within the cell culture bag 10. In addition, in a case of forming the cell culture bag 10 by pasting a plastic film through heat sealing, it is possible to stably form the tubular portions 11 and the communication portions 12 having diameters greater than or equal to 5 mm.

The diameter of a tubular portion or the diameter of a communication portion is a diameter of a circle in a case where the tubular portion or the communication portion has a circular shape, and is set to an average value of a major axis (largest diameter) and a minor axis (smallest diameter) of an ellipse in a case where the tubular portion and the communication portion have an elliptic shape. In addition, in a case where the tubular portion and the communication portion do not have a complete circular shape, the diameter of the tubular portion or the diameter of the communication portion is set to an average value of diameters of the tubular portion or the diameters of the communication portion in all circumferential directions. Furthermore, in a case where the diameters of the tubular portion and the communication portion change in an axial direction, the diameter of the tubular portion or the diameter of the communication portion is set to an average value in all lengths.

The external shape of the cell culture bag 10 is set to, for example, a rectangular shape. The seal portion 13 is formed along an outer edge of the rectangular shape. In addition, the cell culture bag 10 has a plurality of seal portions 14 arrayed in a lattice shape in the inside of the seal portion 13. The region of the plurality of tubular portions 11 and the plurality of communication portions 12 is divided by the seal portions 13 and 14. That is, partition walls of the tubular portions 11 and the communication portions 12 are formed by the seal portions 13 and 14. The seal portions 13 and 14 can be formed through a technique, for example, heat sealing.

Through holes 15 are formed in the seal portion 13. The through holes 15 may be used for supporting the cell culture bag 10.

The cell culture bag 10 has ports 16A and 16B provided on one end side and the other end side of each of the tubular portions 11 in the tube axis direction. The ports 16A and 16B have a through hole (not shown in the drawing) through which the inside and the outside of the cell culture bag 10 are allowed to communicate with each other. For example, injection and discharge of a cell suspension or a culture solution, air ventilation within the cell culture bag 10, extraction of cells during culture, or the like can be performed through the ports 16A and 16B. In the present embodiment, the ports 16A and 16B are inserted into a bag main body so as to penetrate the seal portion 13 from one end side in the X-axis direction. Insertion of the port 16A is performed such that a distal end portion thereof enters an end portion region 17A of the cell culture bag 10. Similarly, insertion of the port 16B is performed such that a distal end portion thereof enters an end portion region 17B of the cell culture bag 10. The end portion regions 17A and 17B are regions which allow communication between the tubular portions 11 on one end side and the other end side of the tube axis direction (Y-axis direction) of each of the tubular portions 11. The ports 16A and 16B are disposed between plastic films while, for example, pasting the plastic films consisting of the cell culture bag 10, and are welded to the bag main body during the pasting of the plastic films through heat sealing or the like. As shown in FIG. 1, the width of the seal portion 13 on a side on which the ports 16A and 16B are inserted is preferably wider than that of the seal portion 13 on the other side. Accordingly, it is possible to secure the strength of the seal portion 13 and to prevent the ports 16A and 16B from dropping out.

The cell culture bag 10 can be manufactured using the plastic films having flexibility and gas permeability as described above. The plastic films can be manufactured through a well-known manufacturing method such as a solution casting method or a melt extrusion molding method. Here, the direction (X-axis direction) in which the plurality of tubular portions 11 of the cell culture bag 10 are arranged is preferably coincident with a film formation flow direction (Machine Direction: MD) during formation of the plastic films. In general, the quality of the plastic film in the film formation flow direction (MD) is higher in homogeneity than the quality of the film in a width direction (Transverse Direction: TD) orthogonal to the film formation flow direction. Accordingly, it is possible to make gas permeability or other properties be homogeneous between the plurality of tubular portions 11 by making the direction (X-axis direction) in which the plurality of tubular portions 11 are arranged be coincident with the film formation flow direction of the plastic film. That is, it is possible to make the culture environment caused by the quality of the plastic film be homogeneous between the plurality of tubular portions 11.

The cell culture bag 10 is a bag which can form a large capacity culture space which can be applied to, for example, culture of $1 \times 10^{10}$ cells which have been ordered. The length of a tubular portion 11 in the tube axis direction (Y-axis direction) is set to, for example, 500 mm to 700 mm. Considering the production suitability of plastic films constituting the cell culture bag 10 or withstanding pressure of the seal portions 13 and 14 in a case where the cell culture bag 10 is used in a "vertical position" to be described below, the length of the tubular portion 11 in the tube axis direction (Y-axis direction) is preferably less than or equal to 1000 mm. In a case where the length thereof is less than or equal to 1000 mm, it is possible to produce the cell culture bag 10 without joining the cell culture bag in the tube axis direction and to produce the cell culture bag so as to prevent withstanding pressure of films from being insufficient with respect to pressure of a culture solution. In contrast, the length of a tubular portion 11 in a direction (X-axis direction) orthogonal to the tube axis direction, that is, in a direction in which a plurality of tubular portions 11 are arranged can be appropriately set in accordance with the scale of culture and can be set to, for example, 1000 mm to 1500 mm.

Hereinafter, an embodiment of a cell culture method according to the embodiment of the present invention using the cell culture bag 10 will be described.

A culture solution which can be applied to the cell culture method according to the embodiment of the present invention is not particularly limited and all culture solution can be applied. Specific examples thereof include liquid media such as a base medium for mammalian cells (for example, DMEM, DMEM/F-12, MEM, DME, RPMI1640, MCDB104, 199, MCDB153, L15, SkBM, Basal Medium, or E8 base medium), a commercially available culture solution for maintaining stem cells, a base medium for insect cells, a medium for yeast, and a medium for bacteria.

Polymer compounds without cytotoxicity may be added to the culture solution which can be applied to the cell culture method according to the embodiment of the present invention for the purpose of continuously floating cells and/or the purpose of preventing cells from being closely attached to each other. Examples of the polymer compounds added to the culture solution for the above-described purposes include a polymer compound that adjusts a specific gravity of a culture solution, a polymer compound that adjusts viscosity of a culture solution, and polymer compounds that form a three-dimensional network structure in a culture solution. Examples of such polymer compounds include polysaccharides such as cellulose, methylcellulose, carboxymethyl cellulose, gellan gum, deacylated gellan gum, hyaluronic acid, alginic acid, carrageenan, xanthan gum, diutan gum, starch, and pectin; proteins such as collagen and gelatin; synthetic polymers such as polyethylene glycol and polyvinyl pyrrolidone.

Various types of generally addable components, for example, antibiotics such as penicillin and streptomycin; vitamins or vitamin derivatives such as ascorbic acid and retinoic acid; sugar sources such as glucose; amino acids; mineral salts; serum or serum substitutes; proteins such as transferrin; hormones such as insulin; growth factors; differentiation inhibitory factors; antioxidants such as 2-mercaptoethanol and dithiothreitol; metal ions such as a calcium ion, a magnesium ion, a zinc ion, an iron ion, and a copper ion may be added to the culture solution which can be applied to the cell culture method according to the embodiment of tie present invention.

In the cell culture method according to the embodiment of the present invention, cells to be cultured are not particularly limited, and all cells such as animal cells, plant cells, fungal cells, bacterial cells, protoplast, established cell lines, and artificially genetically modified cells can be cultured.

An example of cells to be cultured is stem cells. The stem cells are not particularly limited as long as the stem cells have self-replication potency and differentiation potency, and may be pluripotent stem cells or somatic stem cells.

The pluripotent stem cells are cells having self-replication potency and multiple differentiation potency which enables cells to be differentiated into all of an ectoderm, a mesoderm, and an endoderm. Examples of the pluripotent stem cells include embryonic stem cells (ES cells), induced pluripotent stem cells (iPS cells), embryonic germ cells (EG cells), embryonal carcinoma cells (EC cells), multipotent adult progenitor cells (MAP cells), adult pluripotent stem cells (APS cells), and multi-lineage differentiating stress enduring cells (Muse cells).

Examples of the somatic stem cells include mesenchymal stem cells, hematopoietic stem cells, and neural stem cells.

Other examples of cells to be cultured include somatic cells constituting a living body and progenitor cells thereof. Specific examples thereof include lymphocytes, neutrophils, monocytes, megakaryocytes, macrophages, fibroblasts, basal cells, keratinocytes, epithelial progenitor cells, pericytes, endothelial cells, adipose progenitor cells, myoblasts, osteoblasts, chondrocytes, hepatic parenchymal cells, pancreatic β cells, and gliocytes.

Other examples of cells to be cultured include animal cells such as CHO, COS, HeLa, HepG2, C127, 3T3, BHK, HEK293, and Bowes melanoma cells; insect cells such as *Drosophila* S2 and Spodoptera Sf9; fungal cells such as yeast and *Aspergillus*; bacterial cells such as *Escherichia coli* and *Bacillus subtilis*; and plant cells and callus. These cells may be cells into which a protein expression vector is introduced for the purpose of mass expression of proteins.

Primary culture cells or subculture cells which have been cultured using a culture container, such as a dish or a flask, which is used for small-volume culture are collected from the culture container and are suspended in a culture solution to prepare a cell suspension so as to obtain a predetermined cell density. Cells are cultured by injecting a predetermined amount of this cell suspension into the cell culture bag 10 of the present invention.

The cell culture bag 10 is supported such that tube axis directions of the tubular portions 11 are arranged along, for example, a vertical direction during cell culture. That is, the cell culture bag 10 is used in a so-called "vertical position" state in the culture method according to the present embodiment. At this time, for example, the port 16A and the end portion region 17A are disposed on an upper side in the vertical direction and the port 16B and the end portion region 17B are disposed on a lower side in the vertical direction. The cell culture bag 10 is supported in a state of being suspended by a support not shown in the drawing, through inserting a hook 32, which is provided in the support, into a through hole 15 provided in the seal portion 13 during culture as shown in, for example, FIG. 2. The method for supporting the cell culture bag 10 is not limited to the above-described method. The cell culture bag 10 may be supported using other supporting members or the like in a case where the through hole 15 is not provided in the cell culture bag 10.

Figure 2:
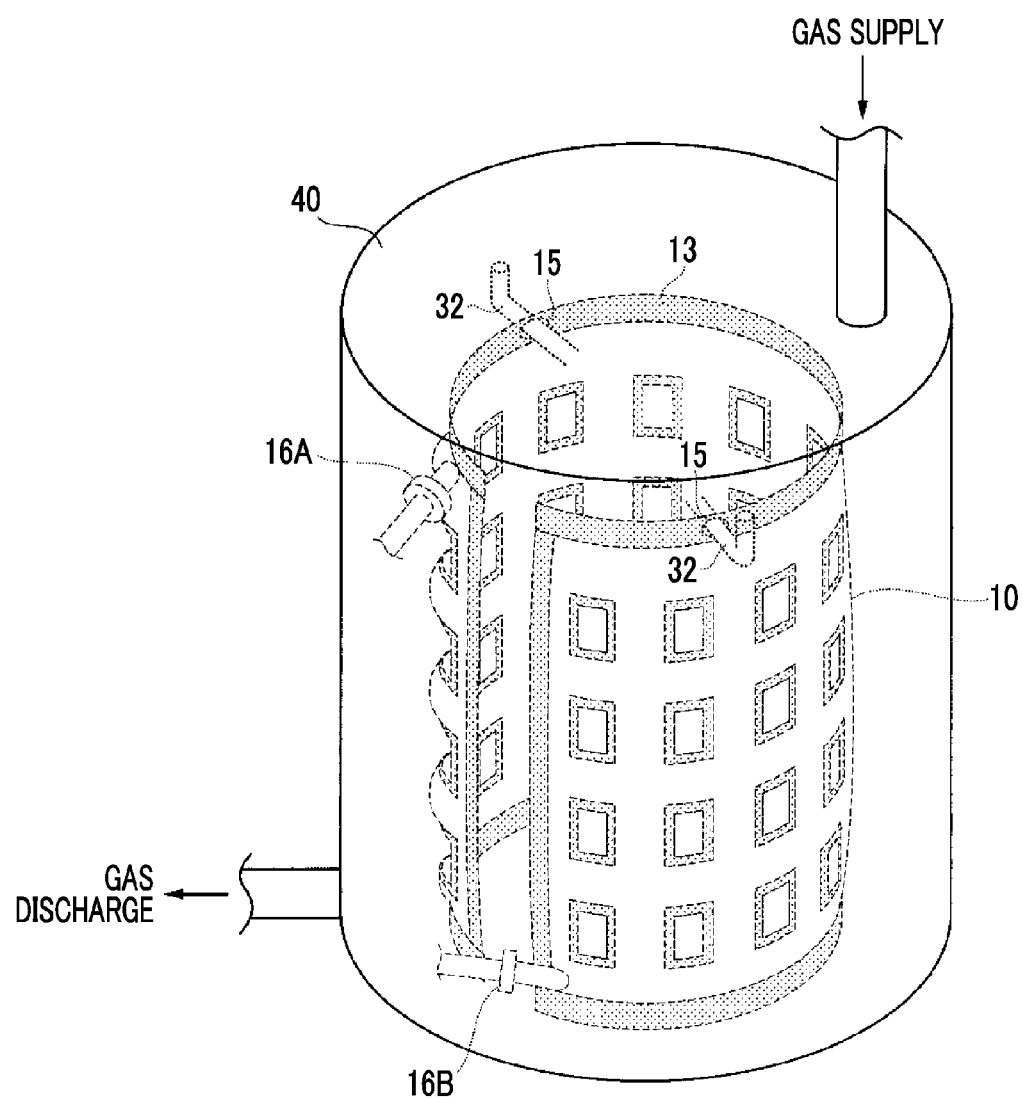
FIG. 2 is a perspective view showing an installation state of the cell culture bag according to the embodiment of the present invention during a culture period.

The cell culture bag 10 is stored in an incubator 40, which is airtightly closed and of which the temperature is controlled to, for example, 30° C. to 40° C. (preferably 37° C.) and the $CO_2$ concentration is controlled to, for example, 2% to 10% (preferably 5%), in a state of being supported so as to be in a vertical position as shown in FIG. 2 during cell culture. In the cell culture method according to the present embodiment, cells are cultured while adding a culture solution in stages. During a culture period, a culture solution is added to the cell culture bag 10 by a predetermined amount for, for example, every 12 hours or 24 hours. The cell culture bag 10 is maintained in a stationary state during the culture period.

In the cell culture method according to the present embodiment, a cell suspension is injected into the cell culture bag through the port 16B disposed on the lower side in the vertical direction. In a case where the cell suspension is injected thereinto through the port 16A disposed on the upper side in the vertical direction, there is a concern that components of a culture solution or cells may be adhered to wall surfaces of tubular portions 11 or communication portions 12 in an upper portion from the liquid surface after the injection of the cell suspension, thereby deteriorating culture efficiency. In a case where the cell suspension is injected through the port 16B disposed on the lower side in the vertical direction, it is possible to prevent deterioration of culture efficiency without adhesion of components of a culture solution or cells on wall surfaces of tubular portions 11 or communication portions 12 in an upper portion from the liquid surface after the injection of the cell suspension. In a case where a cell suspension is injected through the port 16B disposed on the lower side in the vertical direction, it is assumed that the cell suspension is pressurized using a pump or the like. However, in a case where there is a problem in that cells may be damaged due to the pressurization, the cell suspension may be injected through the port 16A disposed on the upper side in the vertical direction. In this case, it is possible to introduce the cell suspension into the cell culture bag 10 without performing pressurization using a pump or the like.

In the cell culture method according to the present embodiment, even in a case of adding a culture solution to the cell culture bag 10 in stages, the culture solution is injected through the port 16B disposed on the lower side in the vertical direction. By adding the culture solution to the cell culture bag through the port 16B, it is possible to prevent adhesion of components of the culture solution on the wall surfaces in an upper portion from the liquid surface after the addition of the culture solution. In addition, in a case of culturing cells through a floating culture method, it is possible to promote mixing of cells with a culture solution through additional injection of the culture solution from the lower side in the vertical direction in a case where the specific gravity of cells is greater than that of the culture solution.

In the cell culture method according to the present embodiment, in a case of first injecting a cell suspension into the cell culture bag 10 and in a case of adding a culture solution to the cell culture bag in stages, the injection of the cell suspension or the culture solution is performed such that the liquid surface reaches upper communication portions 12.

Figure 3A:
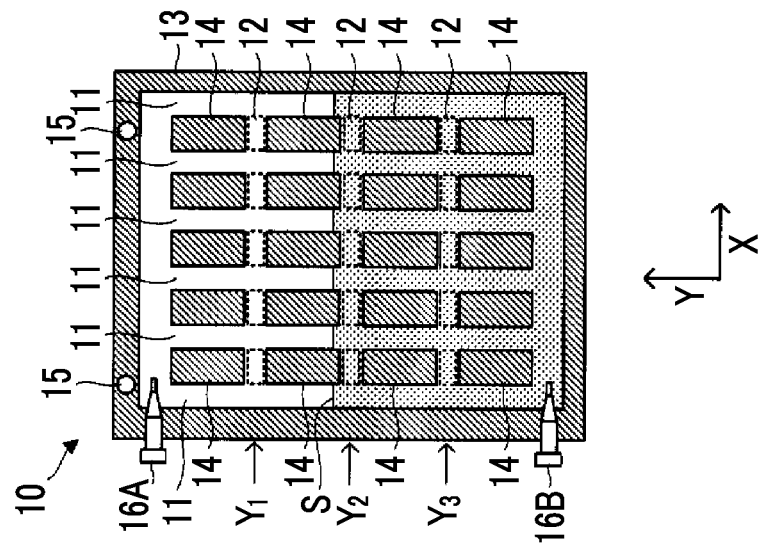
FIG. 3A is a plan view of the cell culture bag according to the embodiment of the present invention after injecting a cell suspension.

For example, in a case of first injecting a cell suspension to the cell culture bag 10, the cell suspension is injected such that the height of a liquid surface S reaches each of the communication portions 12 disposed at a position $Y_3$ in the Y-axis direction as shown in FIG. 3A. Accordingly, the cell suspension stored in each of the tubular portions 11 can be mutually circulated through each of the communication portions 12 disposed at the position $Y_3$.

Figure 3B:
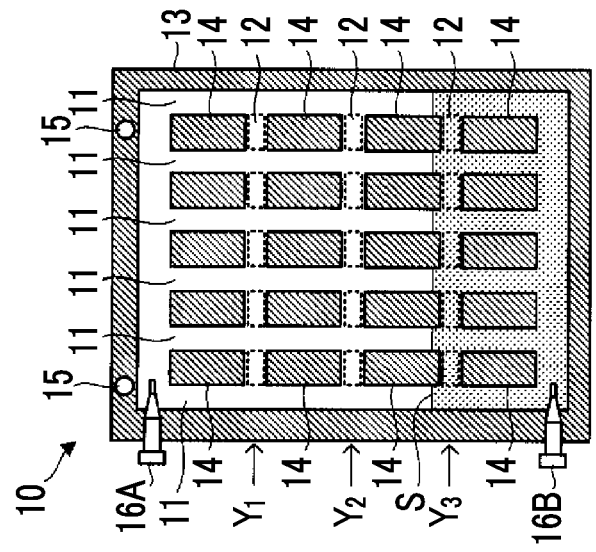
FIG. 3B is a plan view of the cell culture bag according to the embodiment of the present invention after adding a culture solution to the cell culture bag.

Next, after a predetermined period of time has elapsed from the start of culture, a culture solution is added thereto such that the height of the liquid surface S reaches each of the communication portions 12 disposed at a position $Y_2$ in the Y-axis direction as shown in FIG. 3B. Then, after a predetermined period of time has further elapsed, the culture solution is further added thereto such that the height of the liquid surface S reaches each of the communication portions 12 disposed at a position $Y_1$ in the Y-axis direction as shown in FIG. 3C. In this manner, by adding the culture solution such that the height of the liquid surface S reaches the upper communication portions 12, the added culture solution can be mutually circulated through each of the communication portions 12.

In this manner, by injecting the cell suspension or the culture solution such that the liquid surface reaches the upper communication portions 12 while first injecting the cell suspension into the cell culture bag 10 and adding the culture solution thereto in stages, the cell suspension and the culture solution can be mutually circulated through each of the communication portions 12. Accordingly, it is possible to suppress localization of components of the culture solution or the cell density within the cell culture bag 10.

As is clear from the description described above, the cell culture bag 10 according to the embodiment of the present invention has a plurality of tubular portions 11 which have gas permeability and are separated from each other using partition walls. By dividing a storage space in the inside of the cell culture bag 10 into a plurality of tubular spaces in this manner, it is possible to prevent expansion of the bottom portion of the cell culture bag 10 when a cell suspension or a culture solution is stored inside the cell culture bag 10. Accordingly, it is possible to uniformly supply gas over the whole area in the inside of the cell culture bag 10.

In addition, by dividing the storage space in the inside of the cell culture bag 10 into a plurality of tubular spaces, the pressure applied to the seal portions 13 and 14 is dispersed. In addition, in a case of increasing the scale of culture, it is possible to respond to the case by increasing the number of tubular portions 11. That is, according to the cell culture bag 10 of the present embodiment, there is no case where insufficient withstanding pressure of the cell culture bag causes a problem in a case of increasing the scale of culture. Therefore, it is possible to suitably use the cell culture bag for mass culture of cells.

In addition, in the cell culture bag 10 according to the embodiment of the present invention, communication portions 12 are provided in an intermediate region R between two mutually adjacent tubular portions 11 in each pair consisting of the two mutually adjacent tubular portions 11. Accordingly, the cell suspension and the culture solution can be mutually circulated between the plurality of tubular portions 11, and therefore, it is possible to suppress localization of components of the culture solution or the cell density within the cell culture bag 10. That is, according to the cell culture bag 10 of the embodiment of the present invention, it is possible to suppress deterioration in homogeneity of culture environment in a case where the storage space of the cell culture bag is divided into a plurality of regions. In addition, in each pair consisting of two mutually adjacent tubular portions, by setting the number of communication portions 12 provided along the tube axis directions of the tubular portions 11 to two or more, it is possible to promote mutual circulation of an added culture solution between the tubular portions 11 in a case of applying the culture method for adding the culture solution in stages.

According to the cell culture bag 10 of the embodiment of present invention, it is possible to make the culture environment homogeneous between the tubular portions 11. Therefore, homogeneous quality of cultured cells is guaranteed using the cell culture bag 10 and these cells can be regarded as cells at the same lot as each other. That is, cells which can be regarded as cells at the same lot can be cultured by, for example, $1 \times 10^{10}$ cells which have been ordered. Accordingly, it is possible to contribute to realization of, for example, treatment which is performed through cell transplantation and requires a large amount of cells at the same lot as each other which are guaranteed to have uniform quality.

In addition, in the cell culture bag 10 according to the embodiment of the present invention, diameters $D_1$ of the plurality of tubular portions 11 are the same as each other and diameters $D_2$ of the communication portions 12 are designed to be the same as the diameters $D_1$ of the tubular portions 11. In this manner, it is possible to make the culture environment be homogeneous between the plurality of tubular portions 11 by making the diameters of the plurality of tubular portions 11 be the same as each other. In addition, it is possible to equalize the gas supply amount in a central portion of the tubular portions 11 and the communication portions 12 in a radial direction by making the diameters of the tubular portions 11 and the communication portions 12 be the same as each other. It is assumed that cells cultured within the cell culture bag 10 are also distributed in the communication portions 12 as well as in the tubular portions 11. It is possible to eliminate the difference in the culture environment between the tubular portions 11 and the communication portions 12 by making the diameters of the tubular portions 11 and the communication portions 12 be the same as each other. Accordingly, the effect of obtaining homogeneous cells over the entirety of the cell culture bag 10 is promoted.

In addition, in the cell culture bag 10 according to the embodiment of the present invention, the communication portions 12 are disposed at positions $Y_1$, $Y_2$, and $Y_3$ in the Y-axis direction so as to penetrate a plurality of tubular portions 11 in a straight line in the X-axis direction. According to such a configuration, the effect of suppressing localization of components of the culture solution or the cell density within the cell culture bag 10 is promoted in a case of applying the cell culture method for adding a culture solution to the cell culture bag in stages.

In addition, according to the cell culture method of the embodiment of the present invention, the cell culture bag 10 is used in a "vertical position" during cell culture. It is possible to maximize the contact area between the outer surface of the cell culture bag 10 and gas introduced into the cell culture bag 10 using the cell culture bag 10 in a "vertical position", and therefore, the introduction of gas into the cell culture bag 10 is promoted.

In addition, in the cell culture method according to the present embodiment, a cell suspension and a culture solution is injected through the port 16B disposed on the lower side in the vertical direction. Accordingly, it is possible to prevent adhesion of cells or components of the culture solution on an upper portion of the cell culture bag 10 from the liquid surface after the injection of the cell suspension and the culture solution and to suppress deterioration in culture efficiency.

Figure 4:
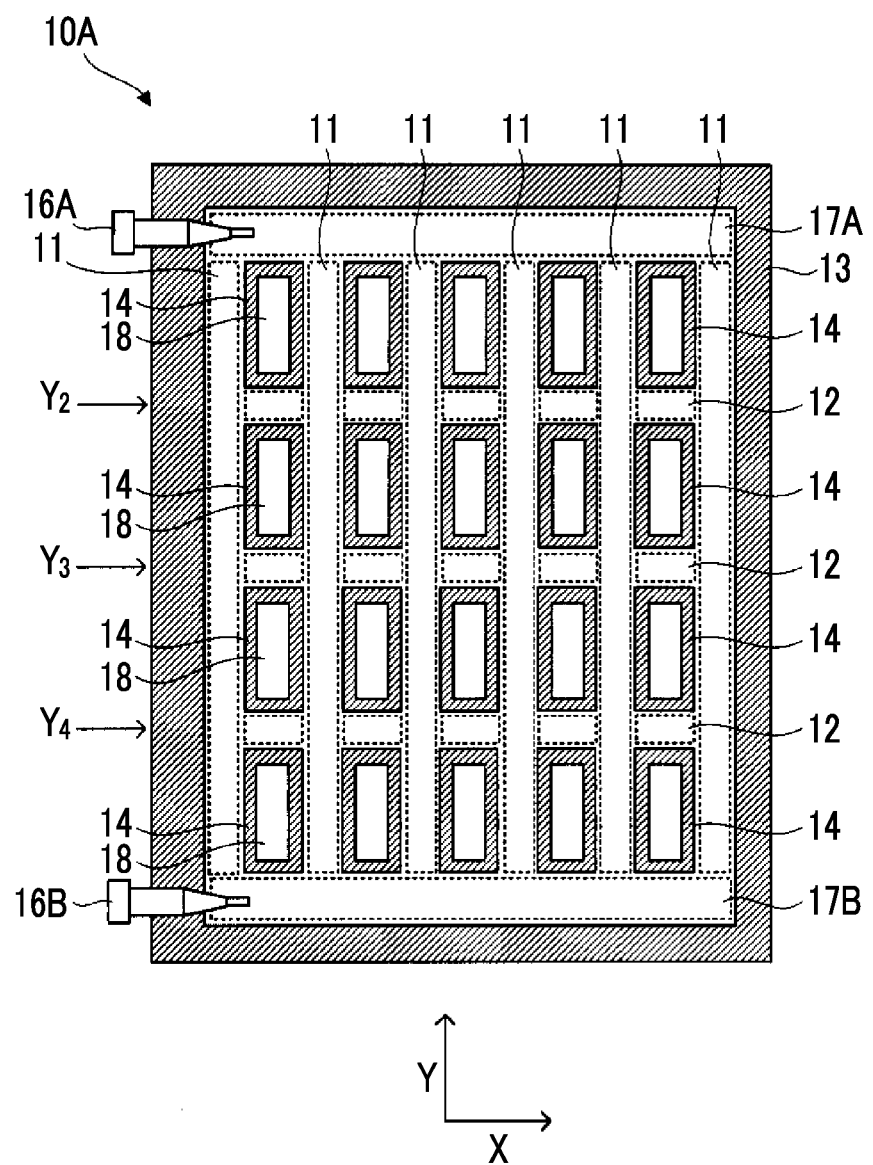
FIG. 4 is a plan view showing a configuration of a cell culture bag according to another embodiment of the present invention.

FIG. 4 is a plan view showing a configuration of a cell culture bag 10A according to another embodiment of the present invention. The same reference numerals will be given to the same or corresponding components of the above-described cell culture bag 10 (refer to FIG. 1) in FIG. 4, and the description thereof will not be repeated. In the cell culture bag 10A, a through hole 18 is provided in each seal portion 14. The shape of the through hole 18 can be set to a rectangular shape along wall surfaces of tubular portions 11 and communication portions 12 as shown in FIG. 4, but is not limited thereto. For example, the shape of the through hole may be set to, for example, a circular shape. Each of the through holes 18 can be used for supporting the cell culture bag 10A as will be described below.

Figure 5:
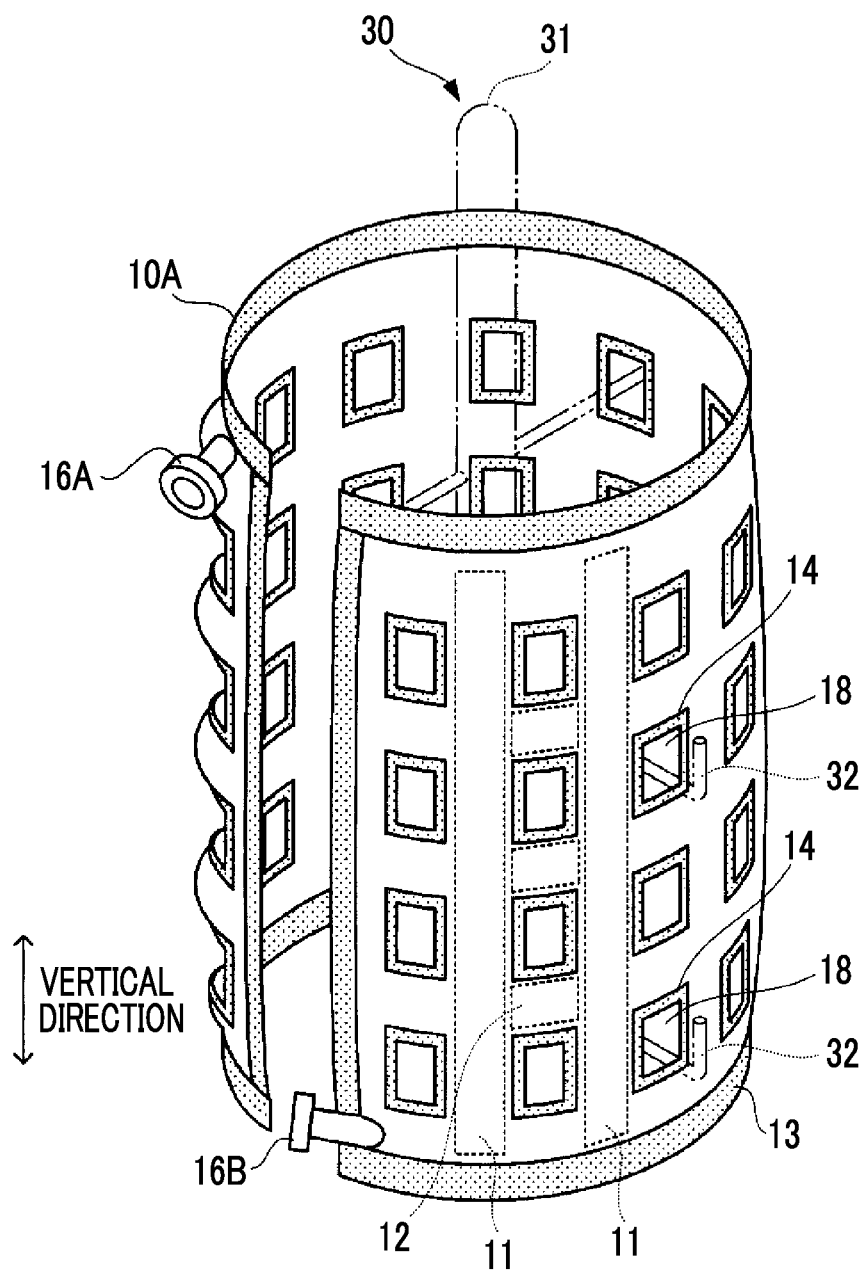
FIG. 5 is a perspective view showing an example of a support state of the cell culture bag according to the embodiment of the present invention during cell culture.
Figure 6:
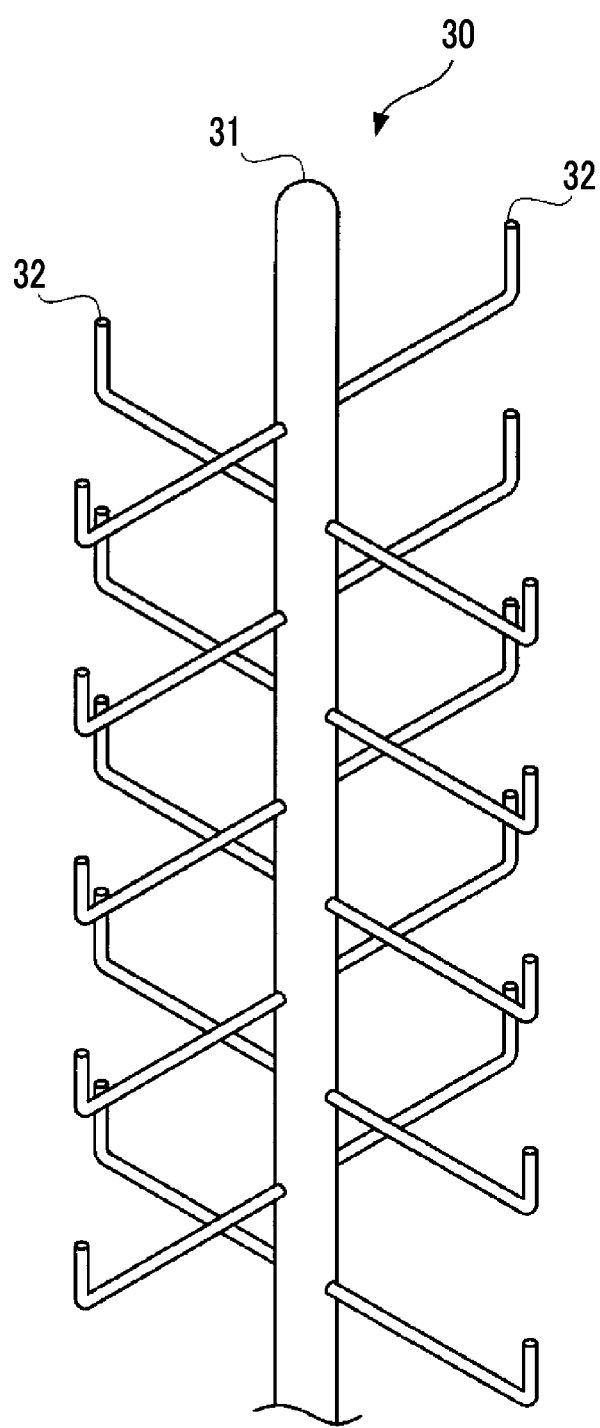
FIG. 6 is a perspective view showing an example of a configuration of a support which supports the cell culture bag according to the embodiment of the present invention.

FIG. 5 is a perspective view showing an example of a support state of the cell culture bag 10A during cell culture. FIG. 6 is a perspective view showing an example of a configuration of a support 30 which supports the cell culture bag 10A during cell culture.

The support 30 has a column portion 31 with a columnar shape and a plurality of hooks 32 provided along a circumferential direction and an axial direction (longitudinal direction) of the column portion 31. The support 30 is disposed such that the axial direction of the column portion 31 follows a vertical direction during cell culture. The cell culture bag 10A is disposed so as to surround the outer circumference of the support 30 in a state where tube axis directions of the tubular portions 11 are directed to the vertical direction during cell culture. At this time, the plurality of hooks 32 are inserted into all or a part of the through holes 18 formed in the seal portion 14 of the cell culture bag 10A. That is, the cell culture bag 10A is fixed to the support 30 is caught by the hooks 32 in a formation portion of the through holes 18. The cell culture bag 10A is supported in a state of being curved in a direction intersecting with the tube axis directions of the plurality of tubular portions 11 such that the plurality of tubular portions 11 are arranged in an annular shape around the support 30.

Figure 7:
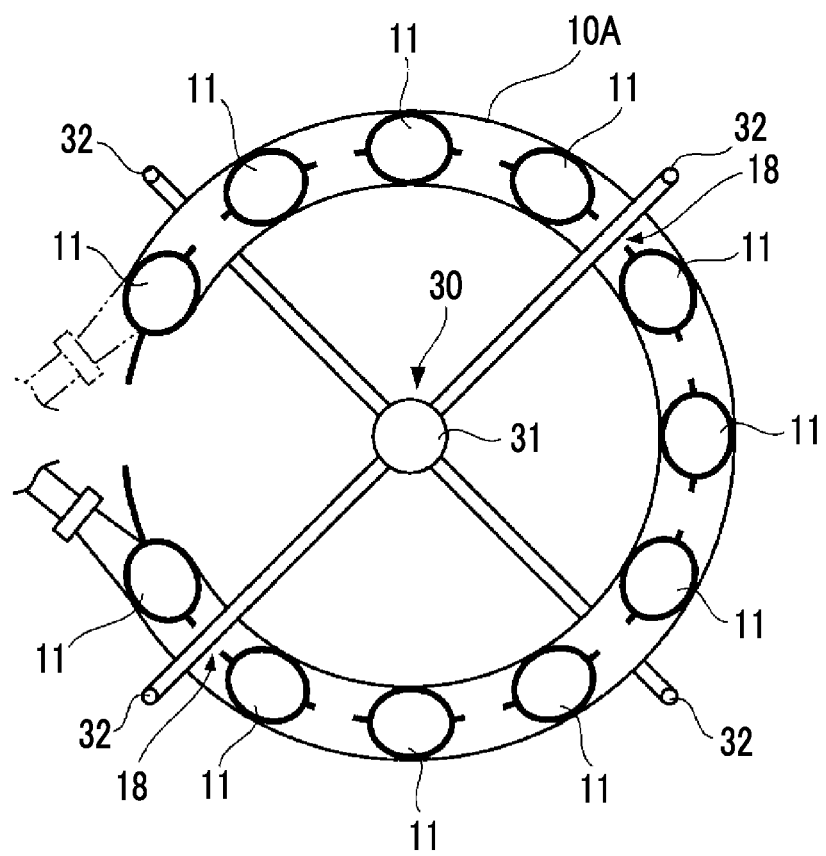
FIG. 7 is a horizontal cross-sectional view of the cell culture bag according to the embodiment of the present invention which has been supported by the support.
Figure 8:
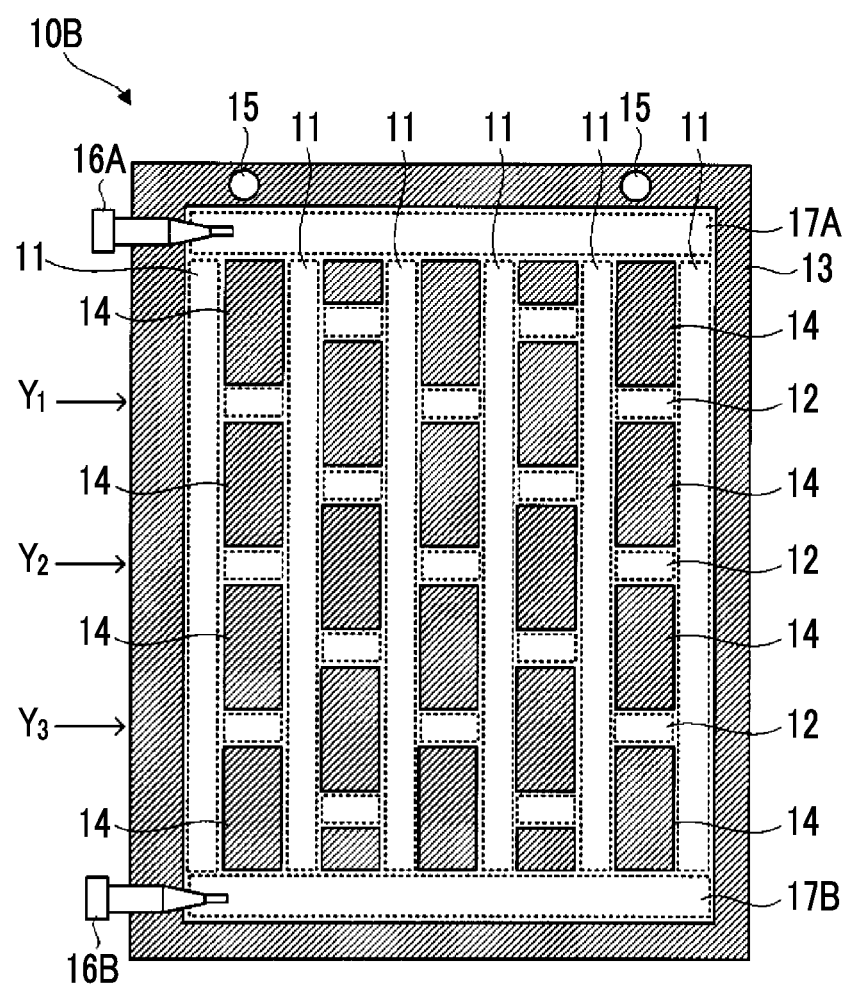
FIG. 8 is a plan view showing a configuration of a cell culture bag according to still another embodiment of the present invention.
Figure 9:
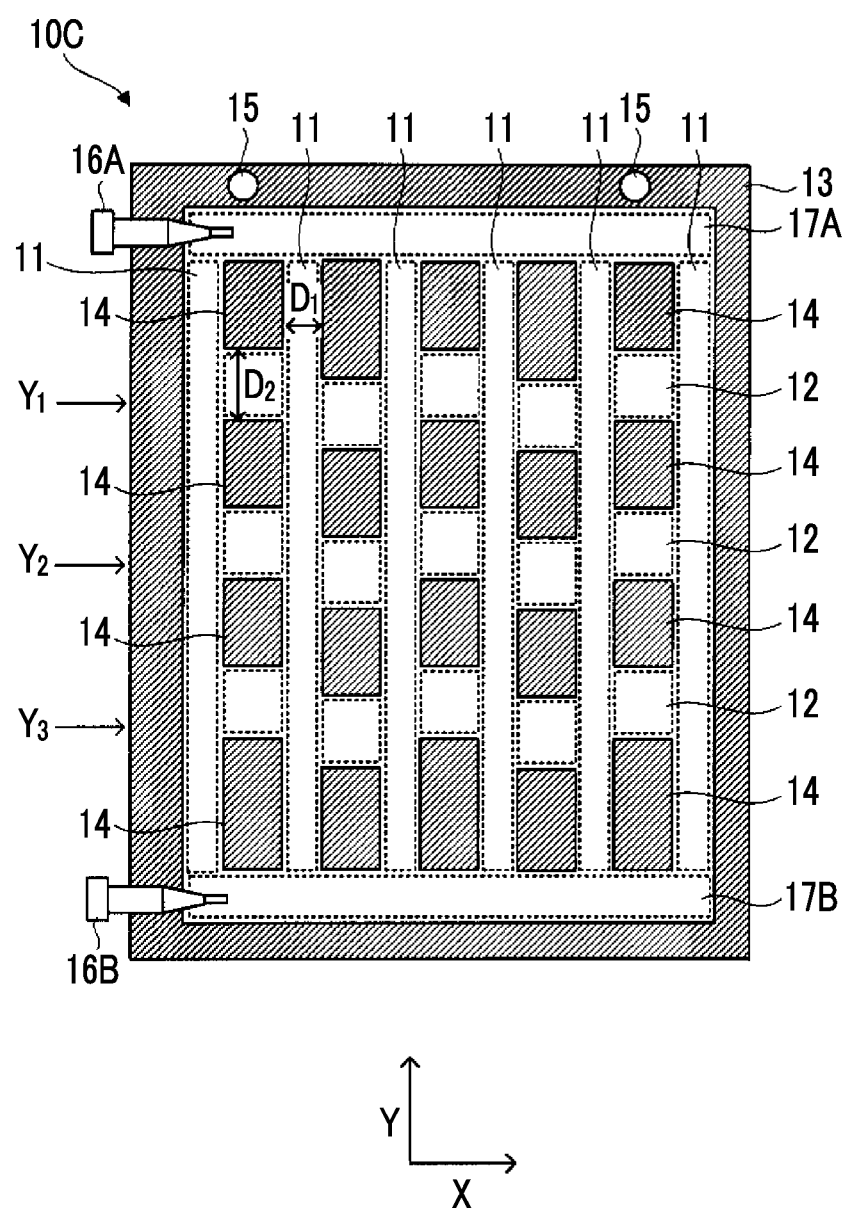
FIG. 9 is a plan view showing a configuration of a cell culture bag according to still another embodiment of the present invention.
Figure 10:
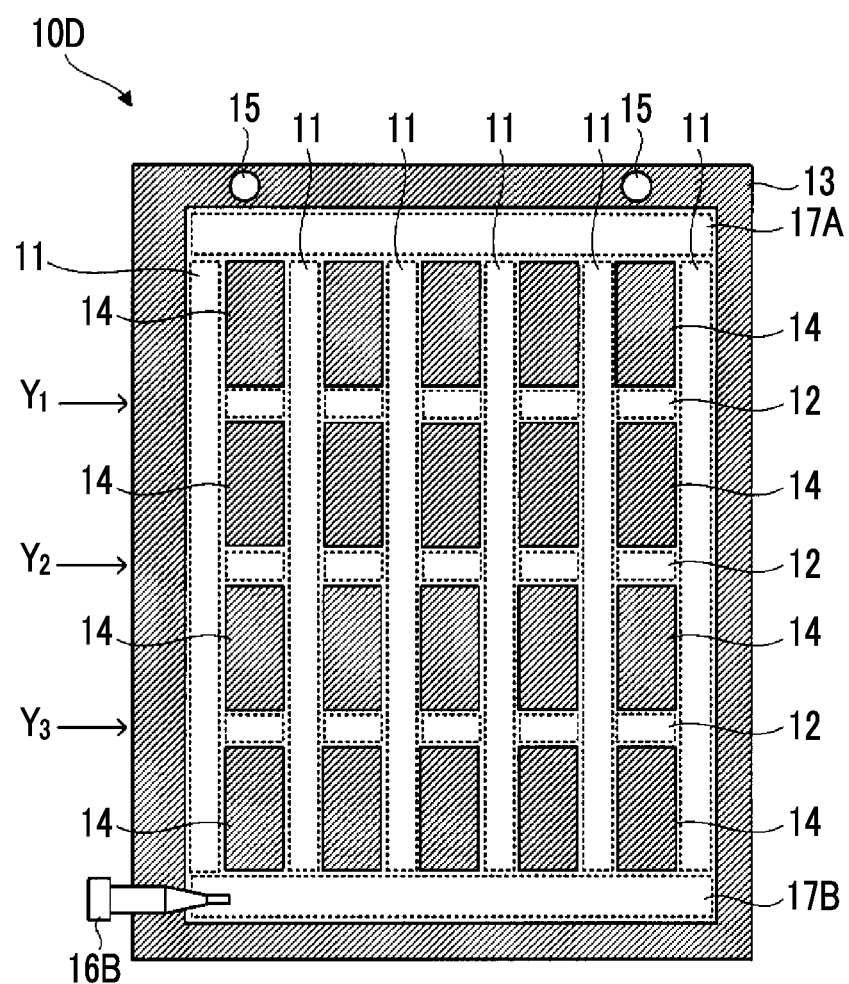
FIG. 10 is a plan view showing a configuration of a cell culture bag according to still another embodiment of the present invention.
Figure 11:
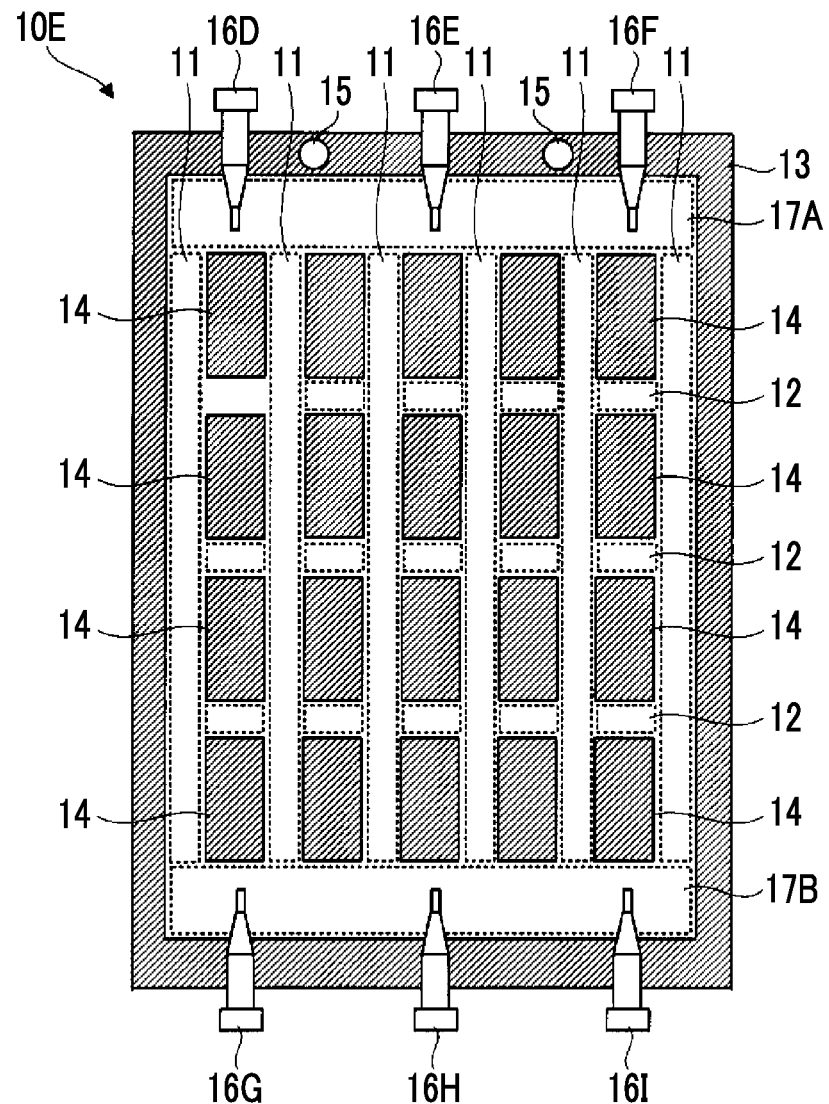
FIG. 11 is a plan view showing a configuration of a cell culture bag according to still another embodiment of the present invention.
Figure 11:
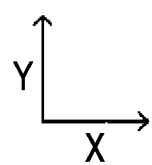
Figure 12:
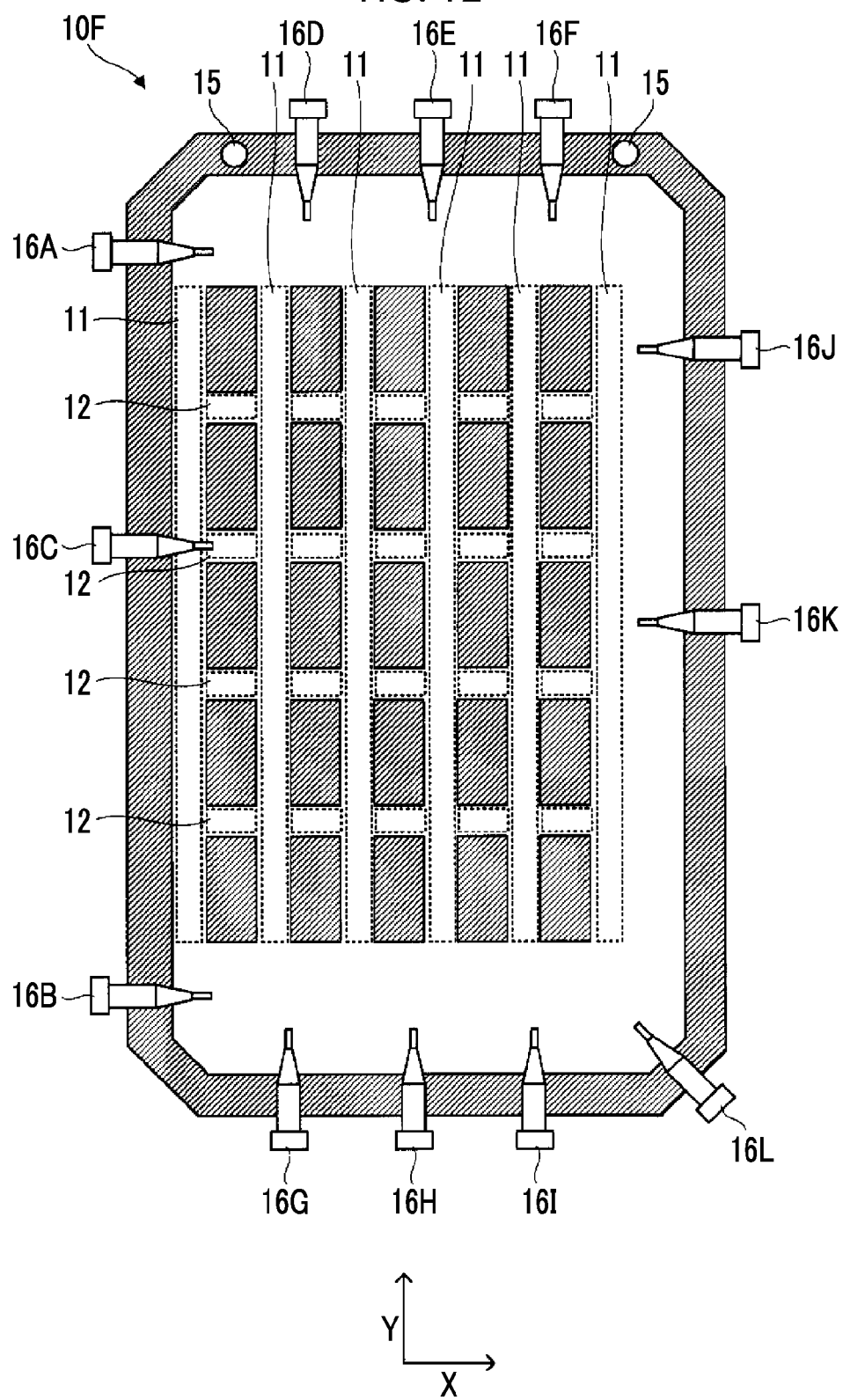
FIG. 12 is a plan view showing a configuration of a cell culture bag according to still another embodiment of the present invention.

FIG. 7 is a horizontal cross-sectional view of the cell culture bag 10A which has been supported by the support 30. In the cell culture bag 10A, it is possible to reduce the weight per insertion portion of a hook 32 by pluralizing places through which the hooks 32 are inserted. In addition, it is preferable that insertion portions of the hooks 32 are disposed in the tube axis directions of the tubular portions 11 and the directions intersecting with the tube axis directions (that is, directions in which a plurality of tubular portions 11 are arranged) without any deviation in order to make the weight in an insertion portion of a hook 32 be homogeneous.

In this manner, it is possible to save the space compared to a case where a plurality of tubular portions 11 are arranged in a straight line, by making the cell culture bag 10A be annularly curved. In addition, it is possible to maximize the contact area between the outer surface of the cell culture bag 10A and gas introduced into the cell culture bag 10A by supporting the cell culture bag 10A in a vertical position using the support 30, and therefore, the introduction of gas into the cell culture bag 10A is promoted. In addition, it is possible to reduce the weight per insertion portion of a hook 32 by pluralizing the through holes 18, and therefore, it is possible to respond to increase of the scale of culture.

FIGS. 8 to 14 are plan views showing configurations of cell culture bags of other embodiments of the present invention. The same reference numerals will be given to the same or corresponding components of the above-described cell culture bag 10 (refer to FIG. 1) in FIGS. 8 to 14, and the description thereof will not be repeated. In the above-described cell culture bag 10 (refer to FIG. 1), the communication portions 12 are disposed at positions $Y_1$, $Y_2$, and $Y_3$ in the Y-axis direction so as to penetrate a plurality of tubular portions 11 in a straight line in the X-axis direction. However, the present invention is not limited to this embodiment. For example, the positions of the communication portions 12 in the Y-axis direction may not be aligned between pairs each consisting of two mutually adjacent tubular portions 11 as in cell culture bags 10B and 10C shown in FIGS. 8 and 9. Even in this case, it is possible to make a cell suspension and a culture solution mutually circulate between a plurality of tubular portions 11, and therefore, it is possible to secure homogeneity of the culture environment. In addition, by making diameters $D_2$ of the communication portions 12 be larger than diameters $D_1$ of the tubular portions 11 as in the cell culture bag 10C shown in FIG. 9, it is possible to promote the mutual circulation of the cell suspension and the culture solution between the plurality of tubular portions 11 and to make the capacity of the cell culture bag 10C be larger than that of the cell culture bag 10.

In addition, the above-described cell culture bag 10 (refer to FIG. 1) has the ports 16A and 16B on both one end side and the other end side of a tubular portion 11 in the tube axis direction. However, the present invention is not limited to this embodiment. Only a port 16B may be provided on one end side of a tubular portion 11 in the tube axis direction as in a cell culture bag 10D shown in FIG. 10. The cell culture bag 10D is provided such that the port 16B is positioned on the lower side in the vertical direction and injection, discharge, and the like of a cell suspension and a culture solution are performed through the port 16B during cell culture. In this manner, it is possible to simplify the configuration compared to that of the above-described cell culture bag 10 by providing only the port 16B on one end side of the tubular portion 11 in the tube axis direction. In contrast, according to the cell culture bag 10, it is possible to perform injection, discharge, and the like of a cell suspension and a culture solution through the ports 16A and 16B on the upper side and the lower side in the vertical direction, and therefore, it is possible to improve flexibility of design of an injection passage and a discharge passage of the cell suspension and the culture solution. The port 16B may be disposed in an intermediate region between one end and the other end of the tubular portion 11.

In addition, the ports 16A and 16B in the above-described cell culture bag 10 (refer to FIG. 1) are inserted into the bag main body from one end side in the X-axis direction. However, the present invention is not limited to this embodiment. For example, ports 16D, 16E, and 16F may be inserted into the bag main body from one end side in the Y-axis direction and ports 16G, 16H, and 16I may be inserted into the bag main body from the other side in the Y-axis direction as in a cell culture bag 10E shown in FIG. 11. In addition, a plurality of ports 16A to 16L may be inserted into the bag main body from one end side and the other end side in the Y-axis direction, one end side and the other end side in the X-axis direction, and corner portions of a cell culture bag 10F as in, for example, the cell culture bag 10F shown in FIG. 12. The ports 16A to 16L can be appropriately used for applications, for example, injection and discharge of a cell suspension and a culture solution, air ventilation within the cell culture bag 10F, and extraction of cells during culture. It is possible to reduce a risk of contamination by providing a plurality of ports 16A to 16L as in the cell culture bags 10E and 10F shown in FIGS. 11 and 12 and assigning specific applications thereto.

Figure 13:
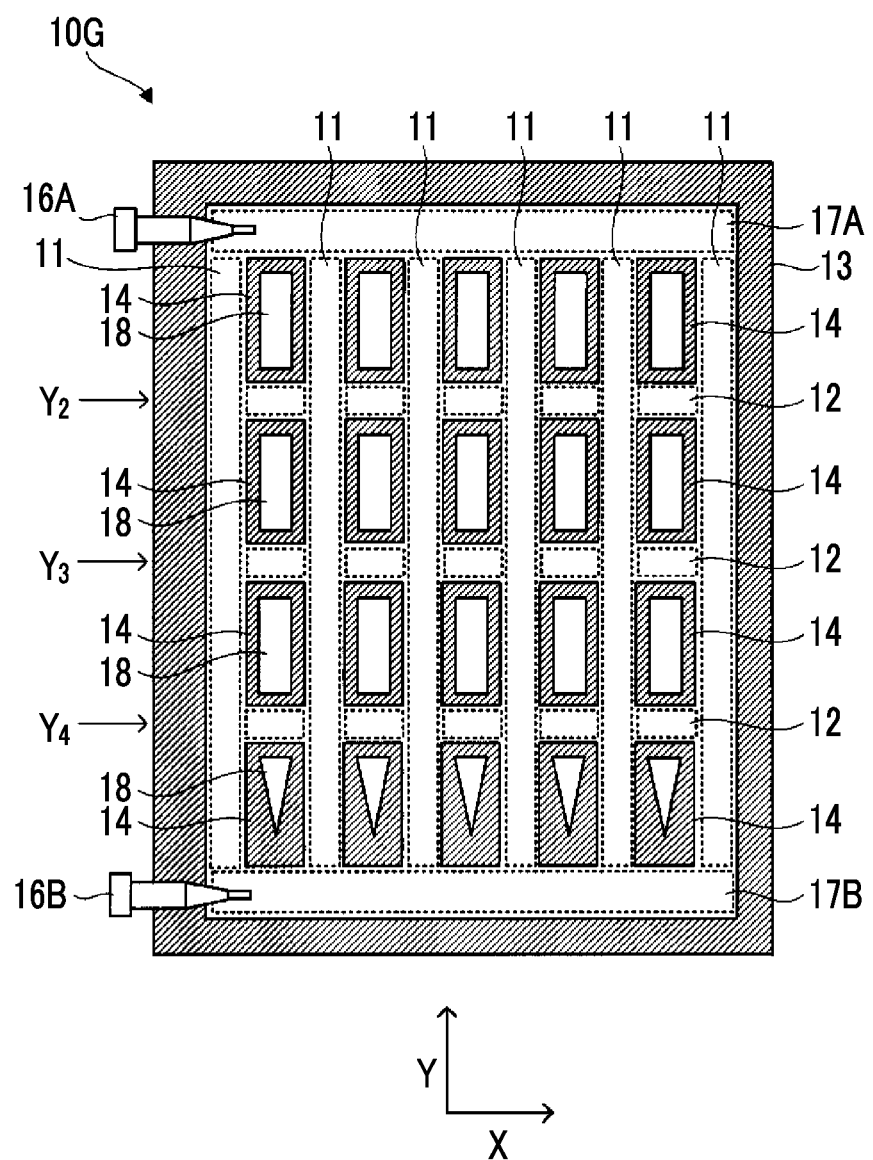
FIG. 13 is a plan view showing a configuration of a cell culture bag according to still another embodiment of the present invention.
Figure 14:
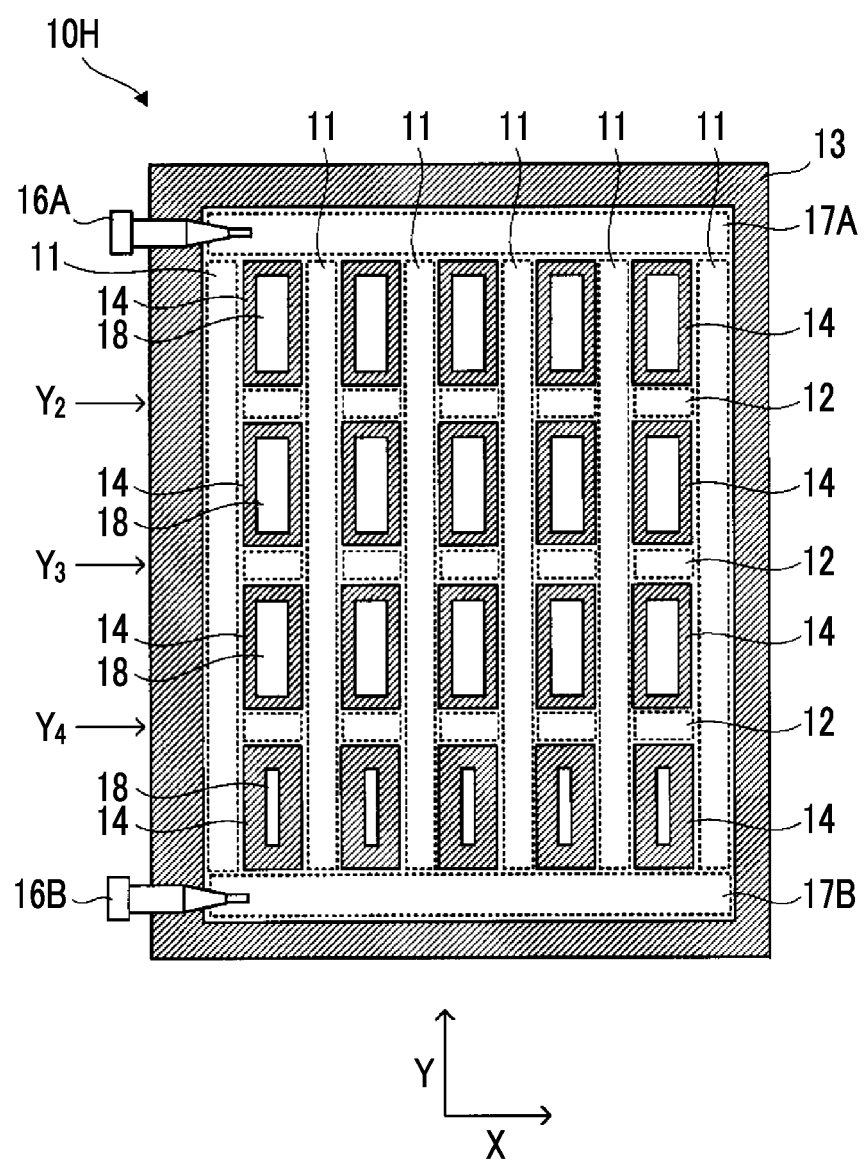
FIG. 14 is a plan view showing a configuration of a cell culture bag according to still another embodiment of the present invention.

In addition, the width of a through hole 18 (the length in the X-axis direction) may be changed along the tube axis direction (Y-axis direction) of a tubular portion 11 as in cell culture bags 10G and 10H shown in FIGS. 13 and 14. In other words, the width of a seal portion 14 in the X-axis direction which is positioned on the lower side in the vertical direction may be made to be wider than that of the seal portion 14 in the X-axis direction which is positioned on the upper side in the vertical direction. For example, the width of a seal portion 14 positioned at the lowermost portion may be enlarged downward in the vertical direction by setting the shape of a through hole 18 formed in the seal portion 14 positioned at the lowermost portion to an inverse triangular shape as shown in FIG. 13. The width of the through hole 18 formed in the seal portion 14 positioned at the lowermost portion may be set to be narrower than that of the through hole 18 formed in the seal portion 14 positioned at the upper portion as shown in FIG. 14. The pressure applied to the seal portion 14 during cell culture becomes large downward in the vertical direction. Therefore, it is possible to increase withstanding pressure of the seal portion 14 positioned on the lower side in the vertical direction by enlarging the width of the seal portion 14 positioned on the lower side in the vertical direction. The width of only the seal portion 14 positioned at the lowermost portion is enlarged in FIGS. 13 and 14. However, the width of a seal portion 14 in an upper portion from the lowermost portion may also be similarly enlarged.

The cell culture bags 10 and 10A to 10H are examples of the cell culture bag in the present invention. The tubular portion 11 is an example of the tubular portion in the present invention. The communication portion 12 is an example of the communication portion in the present invention. The seal portions 13 and 14 are examples of the seal portions in the present invention. The through holes 15 and 18 are examples of the through holes in the present invention. The ports 16A and 16B are examples of the ports in the present invention. The incubator 40 is an example of an airtight container in the present invention. The support 30 is an example of the support in the present invention.

All of the documents, patent applications, and technical standards described in the present specification are incorporated in the present specification for reference to the same extent as a case where incorporation of individual document, patent application, and technical standard for reference is specifically and individually stated.

What is claimed is:

1. A cell culture bag comprising:
   at least three tubular portions having gas permeability, in which a tube axis direction is directed to a first direction, the at least three tubular portions being arranged side by side in a second direction intersecting with the first direction and separated from each other using a partition wall;
   at least three communication portions having gas permeability, the communication portions allowing communication between two mutually adjacent tubular portions of the at least three tubular portions in an intermediate region between one end and the other end of the tubular portions; and
   a plurality of seal portions each having a rectangular shape, the plurality of seal portions partitioning the at least three tubular portions and the at least three communication portions,
   wherein the at least three tubular portions and the at least three communication portions are arranged in a grid arrangement, and the plurality of seal portions are formed at rectangular spaces surrounded by two adjacent tubular portions and two adjacent communication portions, and
   wherein the at least three tubular portions and the at least three communication portions intersect substantially at a right angle.

2. The cell culture bag according to claim 1, wherein diameters of the at least three tubular portions are substantially same as each other.

3. The cell culture bag according to claim 1, wherein diameters of the at least three tubular portions and diameters of the at least three communication portions are substantially same as each other.

4. The cell culture bag according to claim 1, which is formed by pasting a plastic film having gas permeability.

5. The cell culture bag according to claim 4, wherein the partition wall is formed by a plurality of seal portions formed on the plastic film.

6. The cell culture bag according to claim 5, wherein at least one of the plurality of seal portions has a through hole.

7. The cell culture bag according to claim 6,
wherein a width of the through hole changes along the first direction.

8. The cell culture bag according to claim 4,
wherein a film formation flow direction during formation of the plastic film is substantially coincident with the second direction.

9. The cell culture bag according to claim 4,
wherein the plastic film transmits visible light.

10. The cell culture bag according to claim 1,
wherein the diameters of the at least three tubular portions are 5 mm to 50 mm.

11. The cell culture bag according to claim 1,
wherein lengths of the at least three tubular portions in the tube axis direction are shorter than or equal to 1000 mm.

12. The cell culture bag according to claim 1, further comprising:
a port which communicates with each of the at least three tubular portions on at least one end side of each of the at least three tubular portions in the first direction.

13. The cell culture bag according to claim 1, further comprising:
a plurality of ports which communicate with each of the at least three tubular portions on one end side and the other end side of each of the at least three tubular portions in the first direction.

14. A cell culture method using the cell culture bag according to claim 12, the method comprising:
supporting the cell culture bag such that the tube axis directions of the at least three tubular portions follow a vertical direction and at least one port is positioned on a lower side of the vertical direction; and
culturing cells by injecting a cell suspension or a culture solution from the port positioned on the lower side of the vertical direction.

15. The cell culture method according to claim 14,
further comprising adding the culture solution to the cell culture bag by injecting the culture solution from the port positioned on the vertical direction.

16. The cell culture method according to claim 15,
wherein the adding of the culture solution comprises adding to the cell culture bag such that the surface of the culture solution after the addition reaches the position of the heights of the at least three communication portions.

17. The cell culture method according to claim 14,
wherein the supporting of the cell culture bag comprises supporting the cell culture bag in a state where the cell culture bag is curved in a direction intersecting with the tube axis directions of the at least three tubular portions such that the at least three tubular portions are arranged in an annular shape.

18. The cell culture method according to claim 14,
wherein the culturing of the cells comprises culturing the cells while storing the cell culture bag in an airtight container.

19. The cell culture method according to claim 14,
wherein the culturing of the cells comprises culturing the cells while maintaining the cell culture bag in a stationary state during a culture period.

20. A cell culture method using the cell culture bag according to claim 6, the method comprising:
preparing a support that has a hook in a plurality of places in a circumferential direction and an axial direction and of which the axial direction is directed to a vertical direction;
surrounding the outer circumference of the support with the cell culture bag of which the tube axis directions of the at least three tubular portions are directed to the vertical direction; and
culturing cells while supporting the cell culture bag using the support by inserting the hook into the through hole.

21. A cell culture bag comprising:
at least three tubular portions having gas permeability, in which a tube axis direction is directed to a first direction, the at least three tubular portions being arranged side by side in a second direction intersecting with the first direction and separated from each other using a partition wall;
at least three communication portions having gas permeability, the at least three communication portions allowing communication between two mutually adjacent tubular portions of the at least three tubular portions in an intermediate region between one end and the other end of the tubular portions; and
a plurality of seal portions each having a rectangular shape, the plurality of seal portions partitioning the at least three tubular portions and the at least three communication portions,
wherein positions of the at least three communication portions along the first direction are offset between pairs of adjacent tubular portions.

* * * * *